United States Patent [19]
Wang

[11] Patent Number: 5,967,994
[45] Date of Patent: Oct. 19, 1999

[54] METHOD AND SYSTEM FOR CHARACTERIZING THE QUALITY OF SIGNALS INDICATIVE OF HEART FUNCTION

[75] Inventor: Jyh-Yun J. Wang, Newton, Mass.

[73] Assignee: Hewlett-Packard Company, Palo Alto, Calif.

[21] Appl. No.: 09/048,620

[22] Filed: Mar. 26, 1998

[51] Int. Cl.[6] .................................................. A61B 5/0402
[52] U.S. Cl. ............................................................ 600/509
[58] Field of Search ..................................... 600/508, 509, 600/516, 517

[56] References Cited

U.S. PATENT DOCUMENTS

| | | | |
|---|---|---|---|
| 5,224,486 | 7/1993 | Lerman et al. | 600/509 |
| 5,701,906 | 12/1997 | Alcidi et al. | 600/509 |
| 5,779,645 | 7/1998 | Olson et al. | 600/517 |

Primary Examiner—Scott M. Getzow

[57] ABSTRACT

A method and system for characterizing the quality of signals indicative of heart function, where such signals indicative of heart function are derived from electrocardiographic measurements. In the method and system, one or more signals indicative of heart function are measured. In response to the measuring, a noise metric, drawn upon physiologic and non-physiological sources, is created. In response to the creation of the noise metric, the quality of the measured one or more signals is designated.

20 Claims, 11 Drawing Sheets

Fiducial Point Computation

Fiducial Point $(t_{n_0})$ = Initial Reference Point $(t_n)$ + $\Delta$ $$\Delta = \frac{\sum_{k=t_n-18}^{t_n+18} K \cdot [V(t_n + K)]^2}{\sum_{k=t_n-18}^{t_n+18} [V(t_n + K)]^2}$$

METHOD AND SYSTEM FOR CHARACTERIZING THE QUALITY OF SIGNALS INDICATIVE OF HEART FUNCTION

BACKGROUND

1. Technical Field

The present invention relates, in general, to a method and system for providing both quantitative and qualitative assessment of one or more waveform representations of heart function. In particular, the present invention relates to a method and system for providing both quantitative and qualitative assessment of one or more waveform representations of heart function, such as those appearing in one or more leads of the electrocardiograph.

2. Description of Related Art

The present invention presents a method and system for providing qualitative assessment of one or more waveform representations of heart function, such as waveform representations appearing in one or more leads of the electrocardiograph. The present invention provides such qualitative assessment of selected one or more waveform representations of heart function by (1) quantitatively assessing differences in successive QRS complexes making up waveform representations of heart function appearing in one or more leads of the electrocardiograph via the use of a newly invented technique; (2) aggregating the quantitative assessments of the differences of successive QRS complexes making up waveform representations of heart function appearing in one or more leads of the electrocardiograph; and (3) thereafter utilizing the aggregated quantitative assessments to assess the quality of the one or more leads of the electrocardiograph.

One illustrative embodiment of the present invention utilizes certain specific electrical signals derived from a device for monitoring heart function known as the electrocardiograph. In order to understand how these certain specific electrical signals are utilized, it is helpful to have a basic understanding of the electrocardiograph and to what the certain specific electrical signals refer. Accordingly, as an aid to understanding the electrocardiograph, the discussion below presents a brief description of (1) the electrochemical and mechanical operation of the heart, (2) how the electrochemical operation of the heart is transduced into electrical energy which is then used by the electrocardiograph to graphically denote the mechanical operation of the heart, and (3) how the certain specific electrical signals (or "leads" or "channels") are derived from the electrocardiograph.

The mechanical events of the heart are preceded and initiated by the electrochemical activity of the heart (i.e., the propagation of the action potential). There is a device which transforms the electrochemical activity of the heart into a form visible to the human eye: the electrocardiograph, which produces a visual representation of the electrochemical activity of the heart. The visual representation is known as the electrocardiogram (EKG).

During an EKG, electrodes are attached to the body surface. The electrodes are specially treated to allow the charge carriers within the electrodes (electrons) to communicate with the charge carriers within the body (ions) via electrochemical exchange. Attaching electrodes to the body surface allows the voltage changes within the body to be recorded after adequate amplification of the signal. A galvanometer within the EKG machine is used as a recording device. Galvanometers record potential differences between two electrodes. The EKG is merely the recording of differences in voltage between two electrodes on the body surface as a function of time, and is usually recorded on a strip chart. When the heart is at rest, diastole, the cardiac cells are polarized and no charge movement is taking place. Consequently, the galvanometers of the EKG do not record any deflection. However, when the heart begins to propagate an action potential, the galvanometer will deflect since an electrode underneath which depolarization has occurred will record a potential difference from a region on the body under which the heart has not yet depolarized.

A complete heart cycle is known as a heartbeat. On an EKG, a normal heartbeat has a distinctive signal. Initially, the galvanometer notes a relatively short duration rounded positive deflection (known as the P wave), which is caused by atrial depolarization. Subsequent to this, there is a small but sharp negative deflection (known as the Q wave). Next, there is a very large and sharp positive deflection (known as the R wave), after which there is a sharp and large negative deflection (known as the S wave). When the Q, R, and S waves are taken together, they are known as the QRS complex. The QRS complex is caused by ventricular depolarization. Subsequent to the QRS complex, is a relatively long duration rounded positive deflection (known as the T wave), which is caused by ventricular repolarization.

The EKG, in practice, uses many sets of electrodes. But these electrodes are so arranged on the surface of the body such that the signals received will have the similar shape as that just described. Well-known bipolar pairs of electrodes are typically located on a patient's right arm (RA), left arm (LA), right leg (RL) (commonly used as a reference), and left leg (LL). Unipolar electrodes referenced properly are referred to as V leads and are positioned anatomically on a patient's chest according to an established convention (labeled as follows as Leads V1–V6). In heart monitoring and diagnosis, the voltage differential appearing between two such electrodes or between one electrode and the average of a group of other electrodes represents a particular perspective of the heart's electrical activity and is generally referred to as the EKG. Particular combinations of electrodes are called leads. For example, the leads which may be employed in a "gold standard" 12-lead electrocardiogram system are:

Lead I=(LA–RA)
Lead II=(LL–RA)
Lead III=(LL–LA)
Lead aVR=RA–(LA+LL)/2
Lead aVL=LA–(RA+LL)/2
Lead aVF=LL–(LA+RA)/2
Lead V1=V1–(LA+RA+LL)/3
Lead V2=V2–(LA+RA+LL)/3
Lead V3=V3–(LA+RA+LL)/3
Lead V4=V4–(LA+RA+LL)/3
Lead V5=V5–(LA+RA+LL)/3
Lead V6=V6–(LA+RA+LL)/3

Thus, although the term "lead" would appear to indicate a physical wire, in electrocardiography the term actually means the electrical signal taken from a certain electrode arrangement as illustrated above.

Over the years, health care professionals have built up a body of knowledge wherein they have learned to correlate variations in the EKG with different diseases and heart defects. Formally, this process of correlating is known as "electrocardiography."

Electrocardiography, as practiced by human cardiologists, is primarily a visually-oriented art in that the human cardiologists visually inspects a waveform tracing of electrocardiographic measurements taken over time, and on the basis of the morphological (i.e., shape) changes of the waveforms making up the waveform over time the human cardiologist makes a diagnosis of heart function. In making such diagnosis, it is essential that the human cardiologist have an accurate waveform representation, derived from the electrocardiographic measurements, of heart function in that inaccuracies in the waveform will give rise to inaccuracies in diagnosis.

The requirement for an accurate characterization of waveform representation is even more critical for mechanized electrocardiography. That is, machines have been created which have automated many of the functions traditionally performed by human cardiologists.

Multi-lead EKG recordings, which provide different views of the electrical working condition of the heart, are essential tools in the accurate assessment of cardiac electrical activity. In the past decade, multi-lead processing has gained great acceptance in computerized diagnostic EKG applications. In exercise or stress testing application, three EKG leads are usually employed for computer analysis. In Holter monitoring, a two-lead recording is often obtained, which not only provides multiple views of conduction disorders and rhythm disturbances but also overcomes recording problems associated with the use of a single lead, such as loss of electrode contact, improper electrode placement, and muscle and electrical artifacts.

More recently, with the development of advanced microprocessor technology and related digital hardware, the use of multiple EKG leads for real-time arrhythmia and ischemia monitoring has also become feasible and is quickly becoming a monitoring standard. Because of the availability of these new technologies, there has been an increasing interest in developing monitoring algorithms which can simultaneously process more than a single EKG lead.

There are two primary ways in which the multi-lead electrocardiograph is typically utilized. The first primary way in which the multi-lead electrocardiograph is typically utilized is to provide an overall picture of heart function, which is obtained by averaging the multiple leads (or signals) into a composite waveform (one example of such utilization being QRS complex detection). Since, as can be seen by the discussion of electrode placement above, the leads each represent different views of the heart function taken at different locations on the body, the averaging of the leads gives an overall view of how the heart is functioning. The second primary way in which the multi-lead electrocardiograph is typically utilized is to view each lead separately (one example of such utilization being morphology analysis). Since, as can be seen by the discussion of electrode placement above, each lead represents different views of the heart function taken at different locations on the body, viewing each lead separately gives a different and unique view of how different regions of the heart are functioning.

One of the key components in any multi-lead monitoring algorithm is the determination of which EKG leads should be included in the processing. Lead selection for a multi-lead monitoring algorithm is essential for the following reasons: (1) despite the increased amount of processing power available in modern monitors, an EKG algorithm still has to share any processing resource with many other functions that the modern monitors have to perform, and, consequently, the amount of the processing resource allocated for the algorithm may therefore put a limit on the total number of EKG leads that such an EKG algorithm can process; (2) it is common to only use a limited subset of leads, since it is generally assumed in the art that many of the EKG leads are highly redundant; and (3) the advantage of processing one or more additional EKG leads can improve performance only if such one or more additional leads processed exhibit high signal quality, and, using leads that have inferior signal quality will actually degrade algorithm performance rather than improve it. From the foregoing (non-exclusive) reasons it can be seen that it is important to develop a method of measuring the quality of the EKG signals. This signal quality measurement may then be utilized in selecting which EKG leads are accurate and thus should be included for multi-lead processing. In addition, such signal quality measure could also be used in determining the weighting of information from different EKG leads for any QRS complex classification that may be necessary.

Clinical experience with current multi-lead monitoring algorithms has shown that noise has been the primary source of quality degradation of EKG leads. Noise that causes the degradation includes both non-physiological and physiological noise. Non-physiological noise is that arising from other than physiological (i.e., in accord with or characteristic of the normal functioning of a living organism) sources. Examples of non-physiological noise sources are 50/60 Hz electric power lines, muscle artifacts (low frequency or high frequency noise arising from the source of muscle twitch), electrode motion artifacts (low frequency or high frequency noise arising from movement of electrodes relative to the body of a patient), and baseline wander (several leads of the electrocardiograph are referenced against a baseline potential arising from a set of three electrodes which are representative of the electric potential of a patient's body, and since this electric potential can vary over time (due to, perhaps, capacitive effects) it can give rise to distortion of the signals, or noise). Examples of physiological noise are axis shift, biphasic QRS morphology, and QRS amplitude variations.

There are a few (not very effective) known techniques for the detection of individual types of non-physiological noise, such as that represented by out of band noise (e.g., 50/60 Hz noise), baseline wander, and high frequency muscle artifacts. However, there is no known technique for the detection of physiological noise. Furthermore, there is no known technique for the detection and/or quantification of composite noise arising from various and sundry combinations of noise sources, be they strictly non-physiological, strictly physiological, or some combination of non-physiological and physiological noise sources. Consequently, there is presently no way to qualitatively assess EKG leads on the basis of such detection of composite noise.

It has been discussed that in order for such multi-lead monitoring techniques to give accurate multi-lead diagnoses, it is important that the quality of EKG leads used for such monitoring be high. It has also been discussed that the primary source of lead degradation is noise arising from combinations of both physiological and non-physiological factors. It has also been noted that at present no ability to assess the quantity of noise arising from such noise sources exists, and, as a consequence, no ability to assess the quality of leads on the basis of the presence or absence of such noise exists.

From the foregoing it is apparent that a need exists for a method and system which can quantitatively assess the presence of noise in one or more leads of an electrocardiograph and which can provide qualitative assessment of one or more electrocardiographic leads utilizing such one or more quantitative assessments.

SUMMARY OF THE INVENTION

It is therefore one object of the present invention to provide a method and system for providing both quantitative and qualitative assessment of one or more waveform representations of heart function.

It is another object of the present invention to provide a method and system for providing both quantitative and qualitative assessment of one or more waveform representations of heart function, such as those appearing in one or more leads of the electrocardiograph.

The foregoing objects are achieved as is now described. A method and system are provided for characterizing the quality of signals indicative of heart function, where such signals indicative of heart function are derived from electrocardiographic measurements. In the method and system, one or more signals indicative of heart function are measured. In response to the measuring, a noise metric drawn, upon physiologic and non-physiological sources, is created. In response the creation of the noise metric, the quality of the measured one or more signals is designated.

The method and system provide an advantage of creating a noise metric, and a resulting quality assessment of signal, which is responsive to combinations of physiological or non-physiological noise which may be present in the signal. The method and system also provide an advantage of being able to accurately assess the noise contained within, and the quality of, QRS complex waveforms which may have both bigeminal and trigeminal components (a bigeminal component is an abnormal rhythm with a ventricular premature contraction following every normal QRS complex; a trigeminal component is an abnormal rhythm with a ventricular premature contraction following every two normal QRS complexes).

The above as well as additional objects, features, and advantages of the present invention will become apparent in the following detailed written description.

BRIEF DESCRIPTION OF THE DRAWINGS

The novel features believed characteristic of the invention are set forth in the appended claims. The invention itself, however, as well as a preferred mode of use, further objects, and advantages thereof, will best be understood by reference to the following detailed description of an illustrative embodiment when read in conjunction with the accompanying drawings, wherein:

DESCRIPTION OF PREFERRED EMBODIMENT

Figure 1:
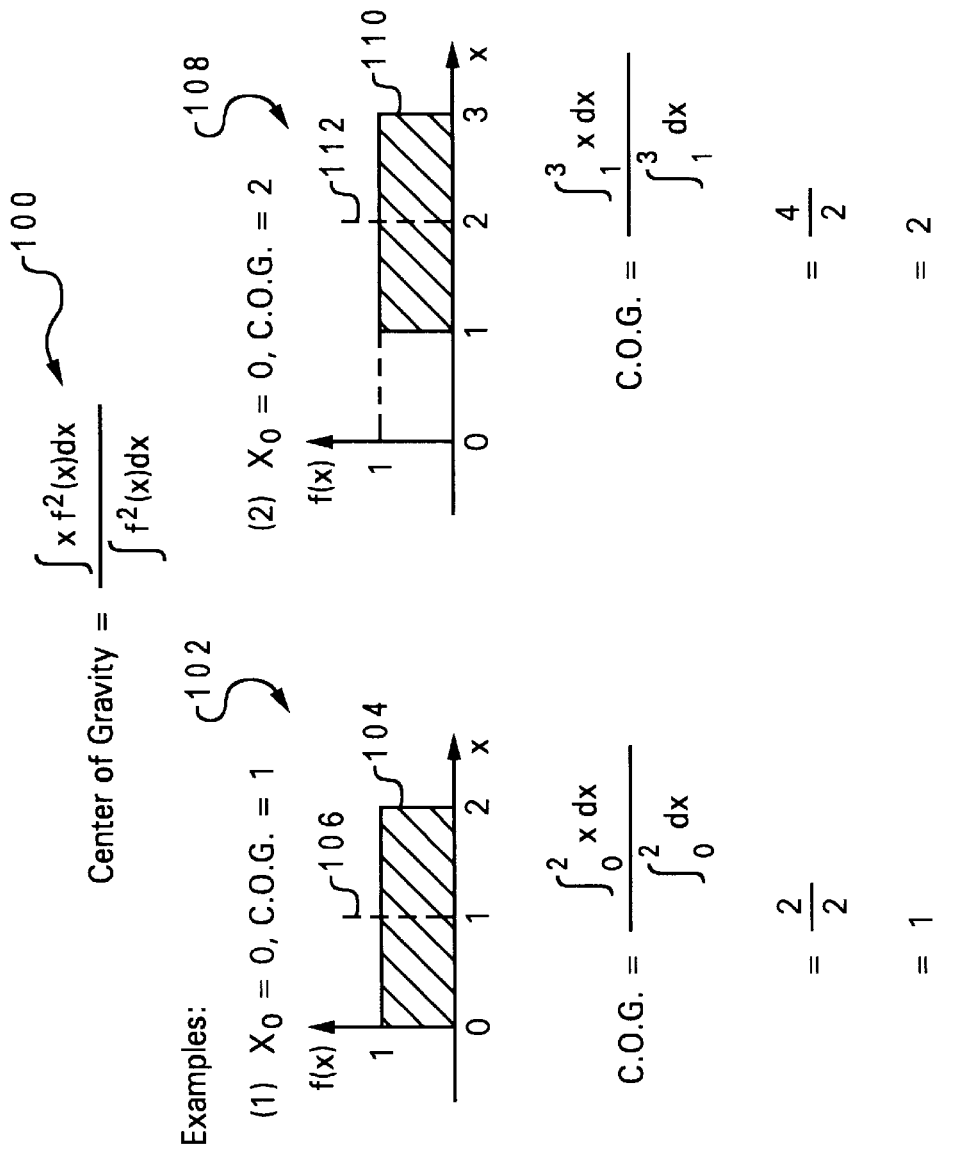
FIG. 1 illustrates the "center of gravity" quantity in its analog form.

The following describes a method and system which utilize electrocardiographic measurements. The method and system are related to the provision of qualitative assessment of one or more waveform representations of heart function, such as those waveform representations appearing in leads of the electrocardiograph.

It will be understood by those in the art that while electrocardiographic leads (i.e., signals) are analog, it is common to time sample each electrocardiographic lead. Accordingly, most of the discussion below deals with such discretely sampled signals; however, in some instances, conceptual clarity will be served in referring to the analog waveforms, and in such instances the discussion will treat the leads utilized by the present invention "as if" they were analog.

One embodiment of the present invention discloses an innovative way of quantitatively assessing the noise (as used in this context, "noise" includes noise arising from physiological and/or non-physiological sources) contained in one or more EKG leads and determining the signal quality of those one or more electrocardiographic leads (i.e., how to determine which leads are "good" quality signals) based on such quantitative noise assessments.

In one embodiment of the present invention, the quantitative assessment of noise contained in any EKG lead (or, equivalently, channel, or signal) is achieved by use of a mismatch indicator which combines various noise sources described in the background section into a single metric. In one embodiment, this metric is computed based on the area differences between successive QRS complexes in the waveform appearing in any lead. (As used herein, the term "successive" means that one complex follows another complex in sequence, and such sequence need not be direct sequence; consequently, a first QRS complex followed by a second QRS complex, a first QRS complex followed by a third QRS complex, a first QRS complex followed by a fourth QRS complex, etc., all would fit under the rubric of "successive" as used herein.) When a lead is essentially noise free, the area differences will be small. On the other hand, if the signal contains significant amounts of noise, the area differences between successive QRS complexes tend to be relatively large, irrespective of whether the noise arises from non-physiological or physiological sources.

In one embodiment, for selected one or more EKG leads, a number of such area differences are calculated over some defined period of time. Thereafter, a signal quality assessment of the selected one or more leads is made on the basis of the characteristics of the statistical distribution of the calculated area differences. For signals that are relatively noise free, the distribution of the area differences will tend to be peaked and the absolute values of the area differences will tend to be small. Conversely, for signals that are relatively noisy, the distribution of the area differences will tend to be spread out and the absolute values of the area differences will tend to be large relative to area differences for relatively noise free signals.

As noted, one embodiment of the present invention utilizes one or more area comparisons between successive QRS complexes in waveforms in one or more selected EKG leads. Those skilled in the art will recognize that such a comparison is not trivial, for the reason that successive electrocardiographic QRS complexes rarely duplicate each other in exact shape or in duration. Consequently, determining how to reference such successive waveform relative to each other is one of the problems involved in such comparison.

The present invention solves this problem by the use of a quantity, known herein as the "center of gravity." This "center of gravity" concept attempts to assess where the majority of energy in each waveform is concentrated along a time axis. After this "center of gravity" has been calculated, it can be utilized to compare the similarity of the morphology of waveforms based upon how those waveforms vary about their respective "centers of gravity." This "center of gravity" point is centroid-like quantity that has been found to function well within the preferred embodiment of the present invention.

Figure 2:
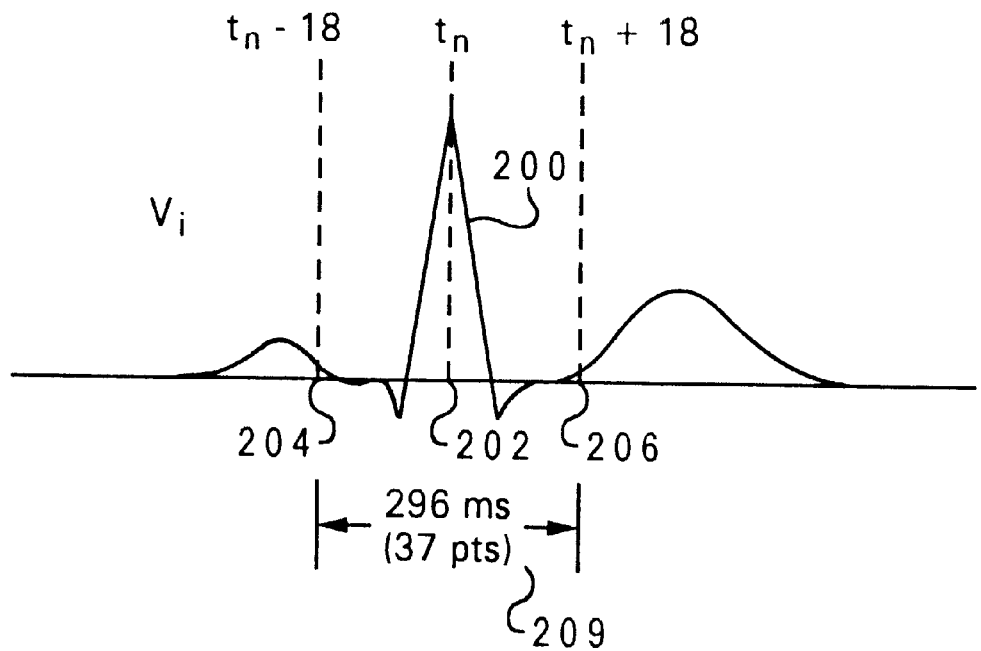
FIG. 2 illustrates how the "center of gravity" concept is applied discretely to calculate the "center of gravity" (fiducial point) of a QRS complex.

Refer now to FIGS. 1 and 2. FIG. 1 presents the "center of gravity" quantity in its analog form. The "center of gravity" quantity is presented in its analog form, because it will facilitate the understanding of the center of gravity quantity so that its discrete version, which will be presented in FIG. 2 and will be utilized by one embodiment, can be easily understood. Shown in FIG. 1 is analog center of gravity equation 100 along with two instances in which the center of gravity has been calculated. In both instances, an initial reference point set at $x_0$=zero (0) has been arbitrarily chosen. In the first instance 102, the center of gravity of rectangular waveform 104 is shown to be calculated at a beginning time of x=zero (0) and an ending time of x=two (2), yielding a center of gravity 106 of rectangular waveform 104 as occurring at x=one (1). In the second instance 108, the center of gravity of rectangular waveform 110 is shown to be calculated at a beginning time of x=one (1) and an ending time of x=three (3), yielding a center of gravity 112 of rectangular waveform 110 as occurring at x=two (2). Thus, FIG. 1 clearly shows that the "center of gravity" can be calculated for a waveform irrespective of its beginning and ending time, and irrespective of its location relative to some arbitrarily chosen reference point $x_0$. With the concept of "center of gravity," in its analog form, now understood it can be shown how it is applied on a discrete time basis in the one embodiment of the present invention.

Refer now to FIG. 2. FIG. 2 shows how the "center of gravity" concept is applied discretely to calculate the "center of gravity" (fiducial point) of a QRS complex. Shown in FIG. 2 is a QRS complex 200. Also shown in FIG. 2 is an initial reference point $t_n$ 202, which essentially constituted a "free choice" (but which in one embodiment of the present invention is chosen to be the peak of an R wave in each QRS waveform as detector by a QRS detector) so long as it lies in the center of some symmetric interval of time samples, which is shown in FIG. 2 as the two-hundred-ninety-six millisecond/thirty-seven point interval 209 spanning left most sample $t_n-18$ 204 to right most sample $t_n+18$ 206. It is to be understood that in the embodiment described, the width of the sample window is two-hundred-ninety-six milliseconds utilized with a sampling rate of one sample taken every eight milliseconds.

The foregoing quantities are utilized in equation 208 to compute delta quantity 210. Thereafter, delta quantity 210 is added to "initial reference point $(t_n)$" 211 (because $t_n$ represents the reference point of the QRS complex, and thus delta 210 is relative to it), to find "fiducial point $(t_{n0})$" 212. As can be seen by comparison of equation 100 with equation 208, "fiducial point $(t_{n0})$" 212 is conceptually the same as the "center of gravity" discussed above, only described in discrete time and when the center of gravity is calculated about a symmetric interval spanning some chosen initial reference point.

FIGS. 1 and 2 have illustrated how each fiducial point is calculated for each individual QRS complex waveform over some interval of time. In one embodiment, two successive QRS complex waveforms are selected. Thereafter a fiducial point is calculated for each of the two selected waves. Subsequently, waveform mismatch is calculated utilizing the two computed fiducial points as the points on each QRS waveform that are to be aligned prior to comparison.

Figure 3:
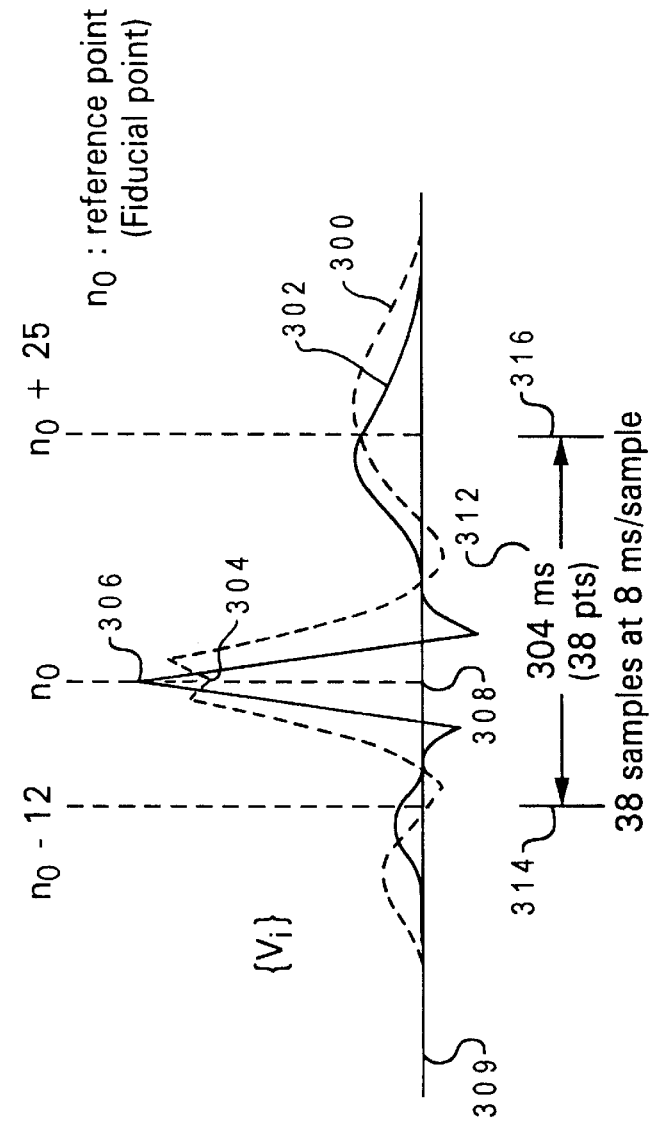
FIG. 3 illustrates both pictographically and mathematically how calculated fiducial points are utilized in one embodiment to calculate waveform mismatch.

Refer now to FIG. 3. FIG. 3 illustrates both pictographically and mathematically how calculated fiducial points are utilized in one embodiment to calculate waveform mismatch. Shown in FIG. 3 are a first EKG waveform 300 and a second EKG waveform 302. Each EKG waveform 300 and 302 has fiducial points 304 and 306, respectively, which it will be assumed have been calculated in accord with the method and system of FIG. 2. As shown, calculated fiducial points 304 and 306 are aligned and thereafter location 308 on the horizontal axis 309 where the aligned fiducial points 304 and 306 are co-located is used as the reference point, such reference point being designated as $n_0$.

Subsequent to the determination of reference point $n_0$, waveforms 300 and 302 are compared for area difference. One embodiment calculates the mismatch between two QRS complexes based upon the area difference between two QRS complexes by use of the normalized absolute value metric, scaled by a factor of five hundred and twelve (512). The preferred embodiment of the present invention calculates the mismatch over a window 312 of thirty eight (38) samples in width, with the left edge 314 of the sample window being defined as twelve (12) samples to the left of reference point $n_0$, and with the right edge 316 of the sample window being defined to be twenty five samples (25) to the right of reference point $n_0$.

In one embodiment, the equation used to represent the mismatch computed over the foregoing noted windows is equation 318. As can be seen by reference to equation 318, the upper and lower edges of the sample window are denoted by the indices on the summations in equation 318. The numerator 320 of equation 318 represents the absolute value of the differences between QRS complexes 300 and 302, and thus for exactly matching QRS complexes numerator 320 would sum to zero (a perfect match), and for exactly opposite QRS complexes numerator 320 would sum to a number of twice the sum of the absolute value of the waveforms. The denominator 322 functions as a normalizing factor, which will be equal to twice the sum of the absolute value of the QRS complexes, thereby serving to normalize equation 318, making the resultant quotient a number between zero (0—a perfect match between QRS complexes) and one (1—mirror opposite QRS complexes). The quotient of equation 318 is then multiplied by a scaling factor of five hundred and twelve to make it more easy to work with, with the result of the multiplication being thereafter referred to as the mismatch indicator 324.

With two fiducial points, and the resulting QRS complex mismatch calculated in the manner explained in relation to FIG. 3, it would seem as if the two comparison of two successive QRS complexes against each other for area differences is complete, and indeed in one embodiment this is the case. However, in another embodiment, it has been found advantageous to "shift" the QRS complex somewhat back and forth about the reference point $n_0$, at which the calculated fiducial points are aligned, in order to attempt to find the minimum amount of mismatch. A straightforward way of finding such minimum mismatch values would be to sequentially shift the waveform a fixed number of samples (e.g. eight samples in either direction), calculate the mismatch value at each shift point, and then select as the minimum calculated values the minimum mismatch between the QRS complexes. However, one embodiment utilizes a more computationally efficient shifting operation. This computationally efficient shifting operation is illustrated in FIG. 4.

Figure 4:
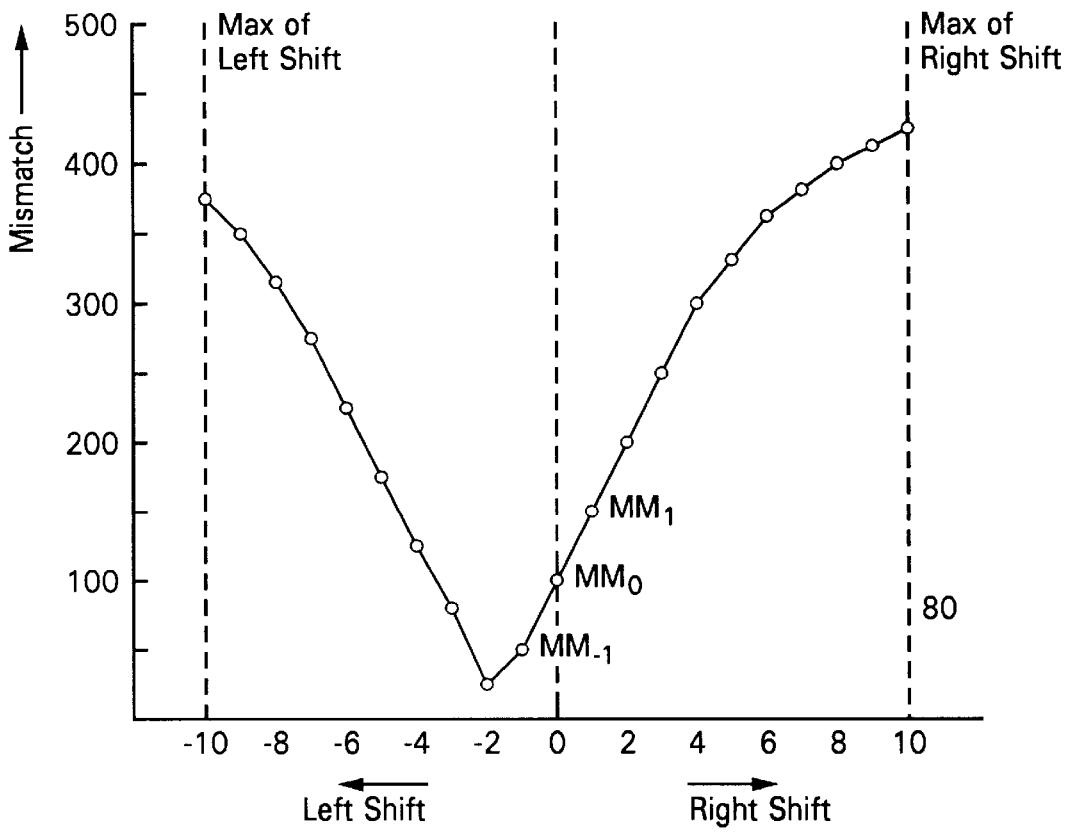
FIG. 4 illustrates the shifting of one waveform relative to the other in a search for the minimum amount of mismatch.

Refer now to FIG. 4. FIG. 4 illustrates the shifting of a first QRS complex relative to a second QRS complex in a search for the minimum amount of mismatch. Shown in FIG. 4 is that, initially, the first QRS complex is shifted relative to the second QRS complex about the reference point $n_0$. The mismatch at the reference point $n_0$ is shown in FIG. 4 as $MM_0$ (mismatch at reference point $n_0$). The mismatch at various points with the first QRS complex shifted relative to the second QRS complex are depicted as $MM_{signed-subscript}$, where "MM" stands for the calculated mismatch between the first QRS complex shifted by the signed integer number of samples (a negative number denotes a left shift, and a positive number denotes a right shift) relative to reference point $n_0$, with the second QRS complex remaining anchored (i.e., unshifted) at reference point $n_0$. For example, $MM_1$ would be interpreted to mean the calculated mismatch between the first QRS complex shifted one sample to the right relative to reference point $n_0$, and with the second QRS complex remaining anchored at reference point $n_0$.

Shown in FIG. 4 is initial shifting logic 400 which illustrates that—with the second QRS complex remaining anchored at reference point $n_0$—the mismatch between the first and second QRS complexes calculated with the first QRS complex is shifted one sample to the left of reference point $n_0$, and the mismatch between the first and second QRS complexes calculated with the first QRS complex is shifted one sample to the right of reference point $n_0$. As is shown in FIG. 4, it if is found that the mismatch at reference point $n_0$ is smaller than either of the mismatches calculated with the waveform shifted one sample to the left or one sample to the right, then the mismatch at the fiducial point is deemed to be the minimum mismatch and thus the mismatch value at reference point $n_0$ (i.e., $MM_0$), is shown as being assigned to $MM_M$ (minimum mismatch value).

Thereafter, shifting logic 402 shows that, in the event that the shift to the left resulted in a calculated mismatch value ($MM_{-1}$) that was less than or equal to both the mismatch value at reference point $n_0$ ($MM_0$) and the mismatch value calculated on the shift to the right, mismatch values calculated upon shifts to the left (e.g., $MM_{-2}$, $MM_{-3}$, $MM_{-4}$, etc.) are thereafter engaged in until such a leftward shift gives an increase in mismatch, at which point the mismatch value recorded prior to the increase in mismatch is recorded as being the minimum mismatch. It should be noted that if all mismatch values are equal (i.e., $MM_{-1}=MM_0=MM_1$) no shifting is done, and if a mismatch value of eighty or below is obtained, shifting is terminated to conserve processing resources.

Shifting logic 404 depicts the event in which a rightward shift resulted in a calculated mismatch ($MM_1$) that was less than the calculated mismatch at reference point $n_0$ ($MM_0$) and less than the calculated mismatch produced by the leftward shift ($MM_{-1}$). Mismatch values calculated upon rightward shifts (e.g., $MM_2$, $MM_3$, $MM_4$, etc.) are thereafter engaged in until such a rightward shift gives an increase in mismatch, at which point the mismatch value recorded prior to the increase in mismatch is recorded as being the minimum mismatch. It should be noted that if all mismatch values are equal (i.e., $MM_{-1}=MM_0=MM_1$) no shifting is done, and if a mismatch value of eighty or below is obtained, shifting is terminated to conserve processing resources.

With the minimum mismatch now known, a cumulative record of mismatches calculated over some time base can be recorded. In the preferred embodiment, the vehicle chosen for such recordation is the histogram, but it will be understood by those within the art that many different cumulative recording vehicles could be utilized.

As has been discussed, in the preferred embodiment, a scaled value is utilized to indicate mismatch, with the number zero (0) indicating that two waveforms compared were virtually identical, and the number five hundred and twelve (512) indicating that the two waveforms compared were virtually mirror opposites in every respect. Consequently, a cumulative record of recorded scaled values can be kept which can then be used to determine the quality of waveform representations of heart function.

One embodiment of the present invention maintains a histogram of the computed area differences of adjacent QRS complexes over a period of time for each lead of interest. Thereafter, the histogram can be utilized directly (e.g., the highest spiked value indicating where the majority of area differences fell, which can then be utilized against some threshold to assess the "noisiness" of a signal) or a cumulative histogram can be derived from the histogram and utilized against some threshold to determine the noisiness of a signal. That is, EKG leads giving histograms with smaller mismatch distributions (that is, with energy concentrated lower on the scale, and the distribution being more "peaked"), or cumulative histograms (that is, with the cumulative energy being concentrated lower on the scale), could be deemed to have better signal quality for automated analysis than those leads with larger mismatch values and/or distributions. In addition to the foregoing it will be recognized by those within the art that several other options are available for utilizing the mismatch measure, such as visual inspection of a histogram, examination of the mode, median, averaging of the histograms for various leads, etc.

Figure 5A:
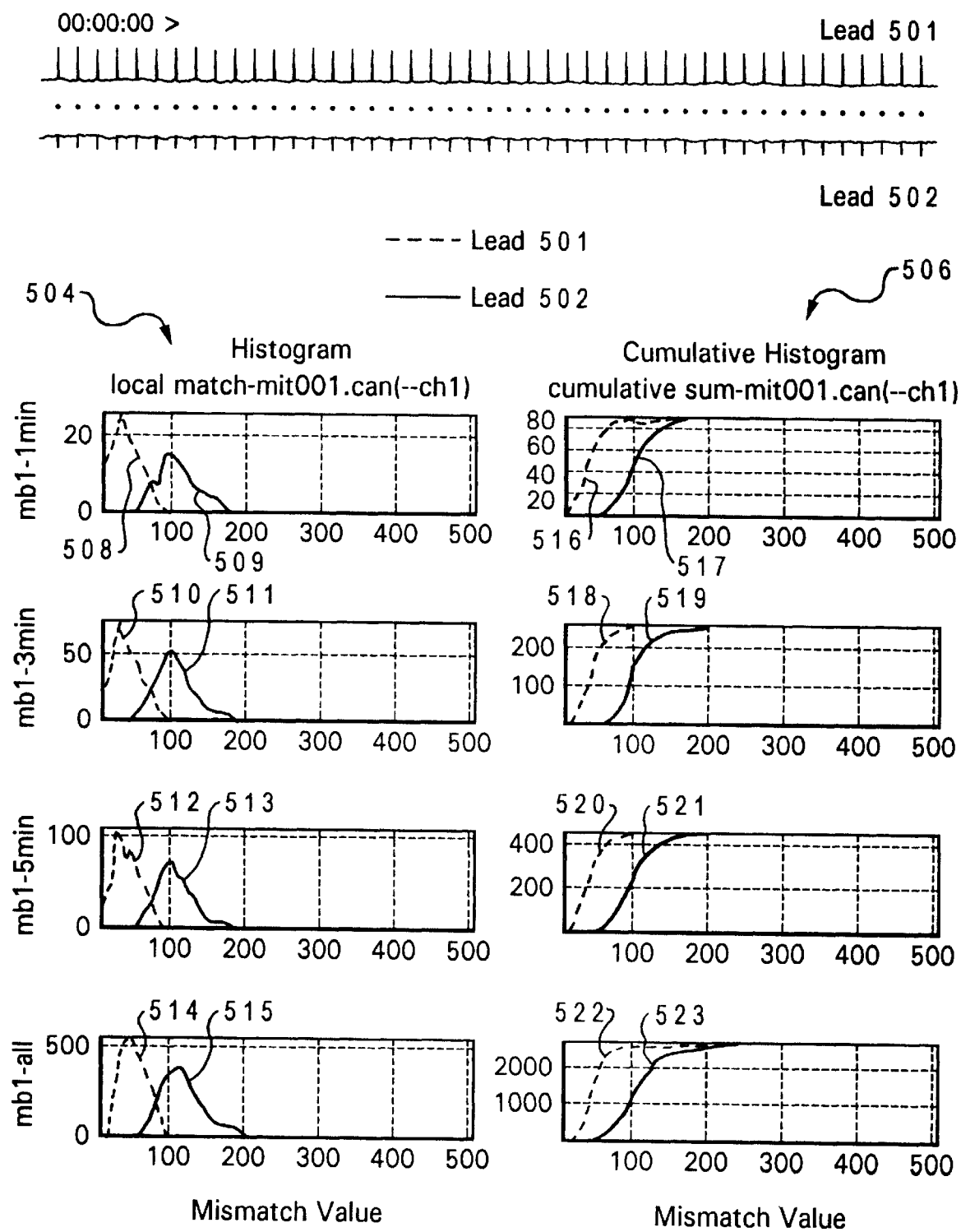
FIG. 5A illustrates input EKG waveform leads with the resultant signal quality measurement presented in both histogram and cumulative histogram form.

Refer now to FIG. 5A. FIG. 5A shows two signals, or waveforms of QRS complexes, where the first signal originates from a first EKG lead and is accordingly labeled lead 501, and where the second signal originates from a second EKG lead and is accordingly labeled lead 502. Below leads 501 and 502 are two columns 504 and 506. Column 504 is illustrative of computed area differences between the complexes appearing directly in sequence on lead 501 and computed area differences between complexes appearing directly in sequence on lead 502. Column 504 is composed of the following: two histograms 508 and 509 of the area differences between directly in sequence successive QRS complexes appearing in waveforms in leads 501 and 502, respectively, based on one minute of data; two histograms 510 and 511 of the area differences between directly in sequence successive QRS complexes appearing in waveforms in leads 501 and 502, respectively, based on three minutes of data; two histograms 512 and 513 of the area differences between directly in sequence successive QRS complexes appearing in waveforms in leads 501 and 502, respectively, based on five minutes of data; and two histograms 514 and 515 of the area differences between complexes appearing directly in sequence on leads 501 and 502, respectively, based on the entire record (thirty minutes) of data. From histograms 508, 510, 512, and 514 one can see by inspection that the majority of lead 501 complexes, over the course of the data run, had a mismatch factor centered somewhere around twenty, with a fairly narrow distribution. As can be seen from histograms 509, 511, 512, and 515 one can see by inspection that the majority of lead 502 complexes, over the course of the data run, had a mismatch factor centered somewhere around one hundred, with a fairly wide distribution. Thus, the inspection of the foregoing noted histograms can be used to determine that the data from lead 501 is not very noisy, while the data from lead 502 is somewhat substantially more noisy.

Column 506 is composed of the following: cumulative histograms 516, 518, 520, and 522 for histograms 508, 510, 512, and 514, respectively; and cumulative histograms 517, 519, 521, and 523 for histograms 509, 511, 513, and 515, respectively. As can be seen from reference to cumulative histograms 516, 518, 520, and 522, about ninety percent of lead 501 mismatch numbers were below about 80 over the course of the run. In contrast, as can be seen from reference to cumulative histograms 517, 519, 521, and 523, respectively, about ninety percent of lead 502 mismatch numbers were below one hundred and twenty over the course of the run.

Those skilled in the art will recognize that many techniques for tracing the behavior of the mismatch factor exist, of which the histogram and the cumulative histogram are only two. Furthermore, those skilled in the art will recognize that there are many techniques available for assessing the significance of the histograms other than visual inspection, such as for example computation of the mean, median, mode, variance, and standard deviation.

Figure 5B:
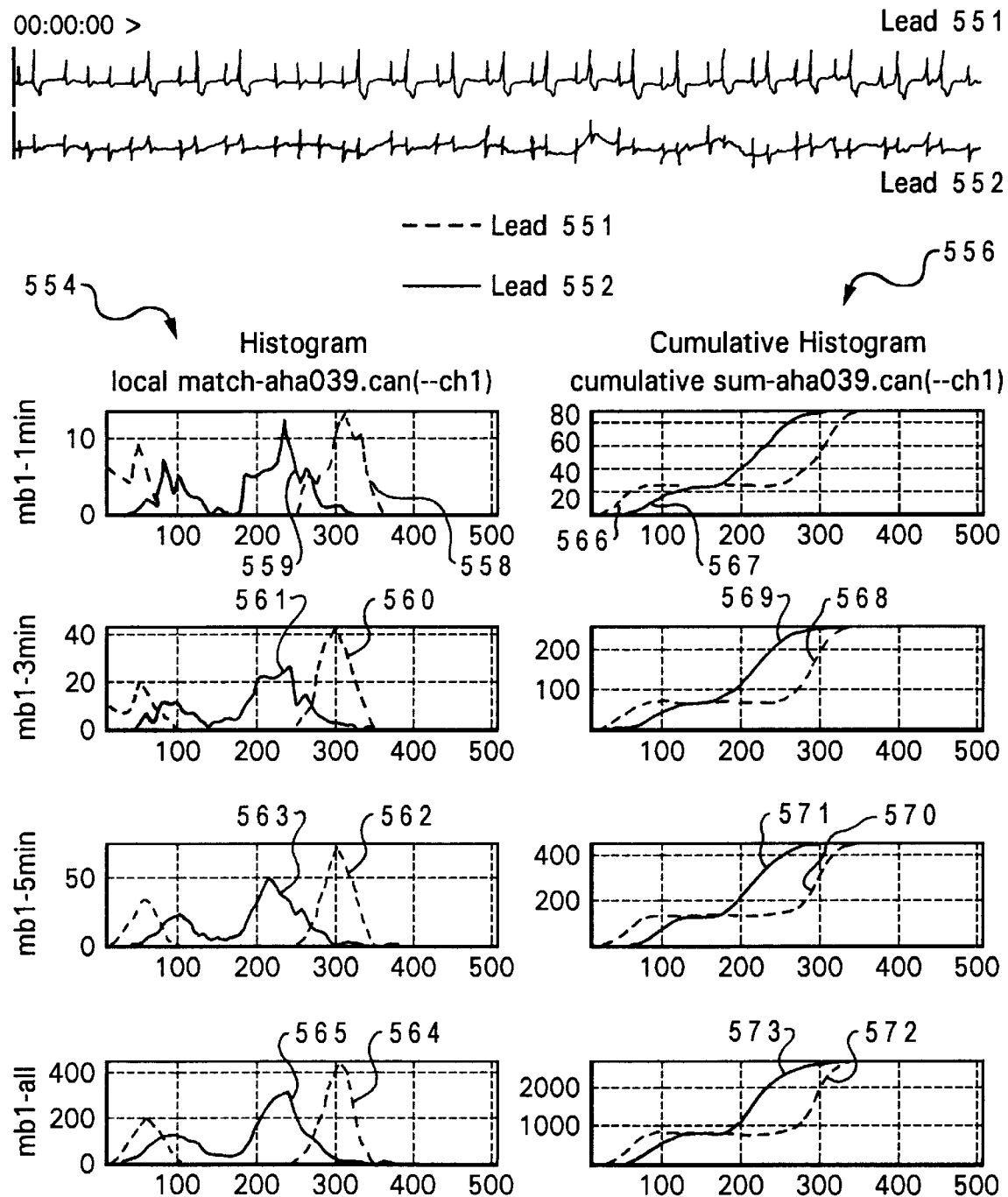
FIGS. 5B and 5C illustrate input EKG waveform leads with resultant signal quality measurement, presented in both histogram and cumulative histogram form, for QRS waveforms directly in sequence and QRS waveforms not directly in sequence.
Figure 5C:
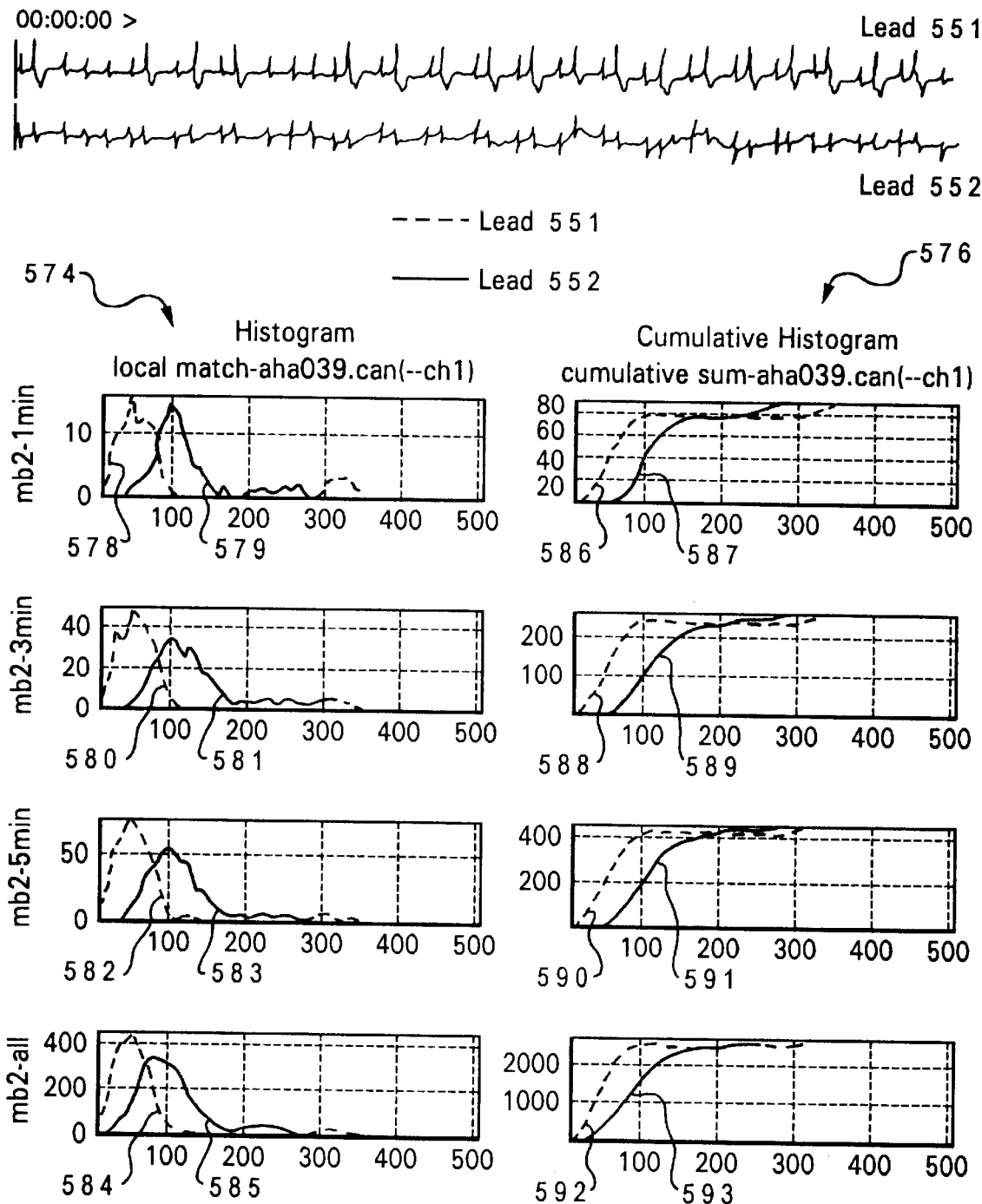

Refer now to FIGS. 5B and 5C. FIGS. 5B and 5C illustrate input EKG waveform leads with resultant signal quality measurement, presented in both histogram and cumulative histogram form, for QRS complexes directly in sequence and QRS complexes not directly in sequence. FIGS. 5B and 5C demonstrate that the fact that one embodiment of the present invention can assess signal quality for both successive QRS complexes which are directly in sequence, and also not directly in sequence, can prove highly useful. Refer now to FIG. 5B. FIG. 5B shows two signals, or waveforms of QRS complexes, where the first signal originates from a first EKG lead and is accordingly labeled lead 551, and where the second signal originates from a second EKG lead and is accordingly labeled lead 552 (it will be recognized by those within the art that leads 551 and 552 exhibit bigeminal patterns). Below leads 551 and 552 are two columns 554 and 556. Column 554 is illustrative of computed area differences between the complexes appearing directly in sequence on lead 551 and computed area differences between complexes appearing directly in sequence on lead 552. Column 554 is composed of the following: two histograms 558 and 559 of the area differences between directly in sequence successive QRS complexes appearing in waveforms in leads 551 and 552, respectively, based on one minute of data; two histograms 560 and 561 of the area differences between directly in sequence successive QRS complexes appearing in waveforms in leads 551 and 552, respectively, based on three minutes of data; two histograms 562 and 563 of the area differences between directly in sequence successive QRS complexes appearing in waveforms in leads 551 and 552, respectively, based on five minutes of data; and two histograms 564 and 565 of the area differences between complexes appearing directly in sequence on leads 551 and 552, respectively, based on the entire record (thirty minutes) of data.

From histograms 558, 560, 562, and 564 one cannot readily discern by inspection that the majority of lead 551 complexes, over the course of the data run, had a mismatch factor truly centered anywhere, nor do such histograms yield much information with regard to the distribution of the histogram. As can be seen from histograms 559, 561, 563, and 565 one cannot see by inspection that the majority of lead 552 complexes, over the course of the data run, had a mismatch truly centered anywhere, nor do such histograms yield much information with regard to the distribution of the histogram. Because of the lack of true centering and unstable distribution, the inspection of the foregoing noted histograms cannot be as easily used to determine the characteristics of the data from lead 551 or lead 552 as were the histograms for leads 501 and 502 discussed in relation to FIG. 5A.

Column 556 is composed of the following: cumulative histograms 566, 568, 570, and 572 for histograms 558, 560, 562, and 564, respectively; and cumulative histograms 567, 569, 571, and 573 for histograms 559, 561, 563, and 565, respectively. As can be seen from reference to cumulative histograms 566, 568, 570, and 572, and from reference to cumulative histograms 567, 569, 571, and 573, respectively, the foregoing cumulative histograms for leads 551 and 552 cannot be as easily used to determine where the majority of the mismatch factors lay as those cumulative histograms for leads 501 and 502 as discussed in relation to FIG. 5A.

Refer now to FIG. 5C. FIG. 5C again shows the two signals, or waveforms of QRS complexes, described in FIG. 5B, where the first signal originates from a first EKG lead and is accordingly labeled lead 551, and where the second signal originates from a second EKG lead and is accordingly labeled lead 552. Below leads 551 and 552 are two columns 574 and 576. Column 574 is illustrative of computed area differences between QRS complexes appearing every third in sequence on lead 551 and computed area differences between QRS complexes appearing every third in sequence on lead 552. Column 574 is composed of the following: two histograms 578 and 579 of the area differences between every third in sequence successive QRS complexes appearing in waveforms in leads 551 and 552, respectively, based on one minute of data; two histograms 580 and 581 of the area differences between every third in sequence successive QRS complexes appearing in waveforms in leads 551 and 552, respectively, based on three minutes of data; two histograms 582 and 583 of the area differences between every third in sequence successive QRS complexes appearing in waveforms in leads 551 and 552, respectively, based on five minutes of data; and two histograms 584 and 585 of the area differences between QRS complexes appearing every third in sequence on leads 551 and 552, respectively, based on the entire record (thirty minutes) of data.

Notice that the fact that mismatches were drawn on third in sequence QRS complexes has given histograms and cumulative histograms that can yield much more information by visual inspection than the histograms and cumulative histograms of FIG. 5B. From histograms 578, 580, 582, and 584 one can see by inspection that the majority of lead 551 complexes, over the course of the data run, had a mismatch factor centered somewhere around twenty, with a fairly narrow distribution. As can be seen from histograms 579, 581, 583, and 585 one can see by inspection that the majority of lead 552 complexes, over the course of the data run, had a mismatch factor centered somewhere around one hundred, with a fairly wide distribution. Thus, the inspection of the foregoing noted histograms can be used to determine that the data from lead 551 is not very noisy, while the data from lead 552 is somewhat substantially more noisy.

Column 576 is composed of the following: cumulative histograms 586, 588, 590, and 592 for histograms 578, 580, 582, and 584, respectively; and cumulative histograms 587, 589, 591, and 593 for histograms 579, 581, 583, and 585, respectively. As can be seen from reference to cumulative histograms 586, 588, 590, and 592, about ninety percent of lead 551 mismatch numbers were below about one hundred (100) over the course of the run. In contrast, as can be seen from reference to cumulative histograms 587, 589, 591, and 593, respectively, about ninety percent of lead 552 mismatch numbers were below one hundred and fifty (150) over the course of the run.

Figure 6:
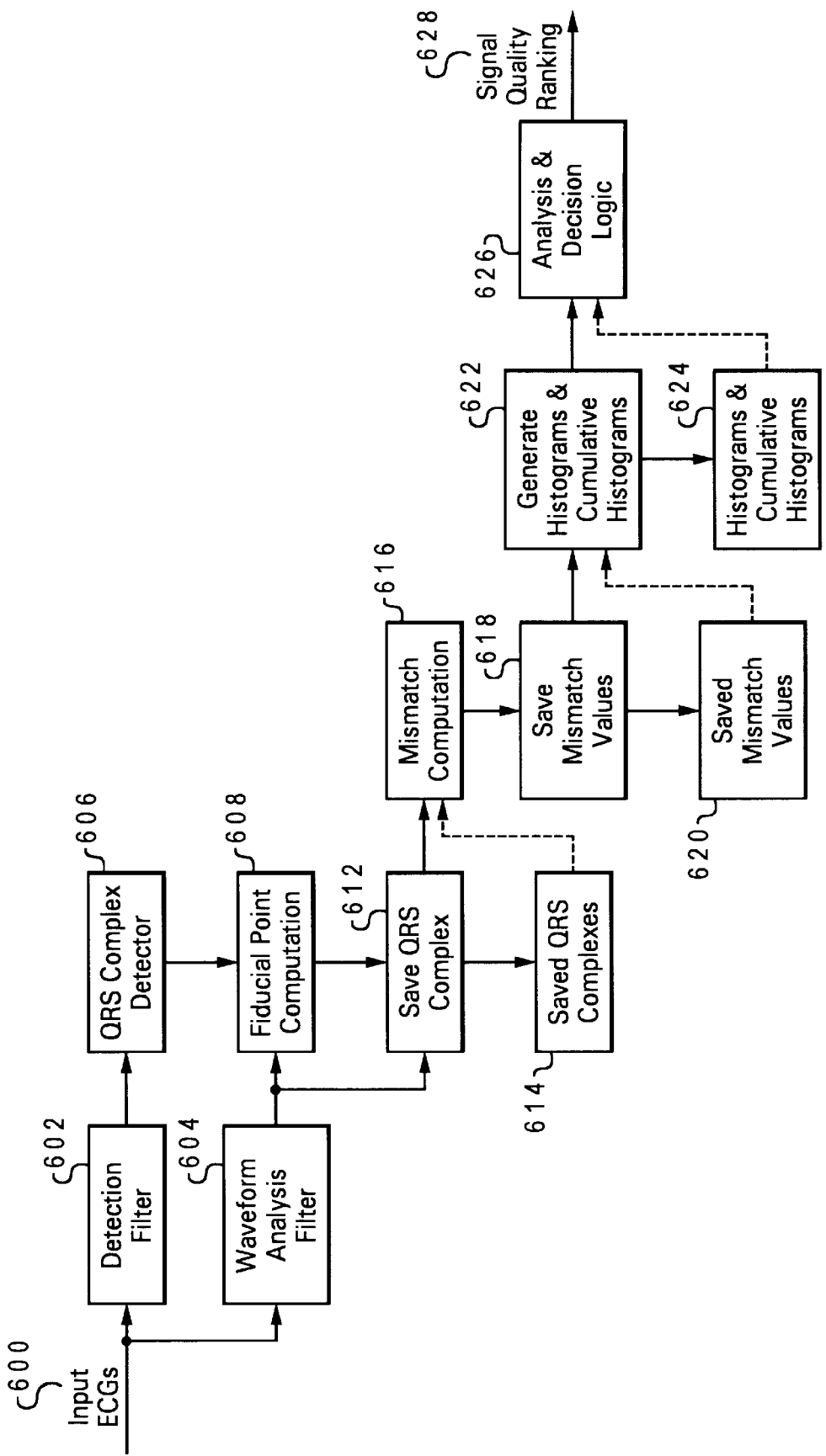
FIG. 6 illustrates a system which can be utilized to implement an embodiment represented by the methods and systems discussed above.

Refer now to FIG. 6. FIG. 6 illustrates a system which can be utilized to implement an embodiment represented by the methods and systems discussed above. Shown in FIG. 6 is input EKG data 600, which can be composed of one or more leads containing EKG data. Input EKG data 600 is virtually simultaneously fed into detection filter 602 and waveform analysis filter 604.

The output (filtered input EKG data) of detection filter 602 is accepted by QRS complex detector 606, which detects the QRS complexes in each stream so that successive QRS complexes can be compared. The output of QRS complex detector 606 is fed into fiducial point computation unit 608.

Fiducial point computation unit 608 accepts input from QRS complex detector 606 and input (filtered input EKG data) from waveform analysis filter 604. Fiducial point computation unit 608 computes the fiducial points for successive waveforms to be compared. The output of fiducial point computation unit 608 is fed into save QRS complex unit 612.

Save QRS complex unit 612 accepts input from waveform analysis filter 604 and fiducial point computation unit 608. Save QRS complex unit 612 deposits the QRS complexes in saved QRS complexes repository 614 and also feeds through the signals received from waveform analysis filter 604 and fiducial point computation unit 608 to mismatch computation unit 616. It has been explained that mismatch computation is performed on successive QRS complexes. How this may be achieved is shown by the dashed line connecting saved QRS complexes repository to 614 and mismatch computation unit 616.

In order to achieve mismatch computation of QRS complexes in succession, it is necessary to have access to earlier stored QRS complexes for comparison against a current QRS complex. In such instances, mismatch computation unit 616 obtains such earlier stored QRS complexes from saved QRS complexes repository 614 as is illustrated by the dashed line connecting saved QRS complexes repository 614 and mismatch computation unit 616.

Mismatch computation unit 616 computes the mismatch between successive QRS complexes appearing in one or more selected leads from the input EKG data 600. Thereafter, the mismatch for the one or more selected leads is sent to save mismatch values unit 618. Save mismatch values unit 618 deposits the mismatch values for the one or more selected leads in saved mismatch values repository 620 and also feeds through the signals received from mismatch computation unit 616 to generate histograms and cumulative histograms unit 622. It has been explained that mismatch computation is performed on QRS complexes in succession, and that histograms and cumulative histograms can be generated by such mismatch computation performed on QRS complexes in succession. How this may be achieved is shown by the dashed line connecting saved mismatch values repository 620 and generate histograms and cumulative histograms unit 622.

In order to achieve histograms or cumulative histograms for mismatch computation of QRS complexes in succession, it is necessary to have access to QRS complexes drawn upon such mismatch computations. In such cases, generate histograms and cumulative histograms unit 622 obtains such earlier stored mismatches from saved mismatch values repository 620, as is illustrated by the dashed line connecting generate histograms and cumulative histograms unit 622 and saved mismatch values repository 620.

Thereafter, generate histograms and cumulative histograms unit 622 sends generated histograms and cumulative histograms (for either and/or both directly in sequence or not directly in sequence QRS complexes) for the one or more selected leads to save histograms and cumulative histograms repository 624 and to analysis and decision logic unit 626. Shown by the dashed line connecting histograms and cumulative histograms repository 624 and analysis and decision logic unit 626 is that analysis and decision logic 626 could also utilize histograms and cumulative histograms drawn on mismatches calculated from earlier QRS complexes by retrieving such from histograms and cumulative histograms repository 624.

Analysis and decision logic unit 626 utilizes the histograms/cumulative histogram data to rank the one or more selected leads on the basis of signal quality, and outputs signal quality ranking signal 628.

Figure 7:
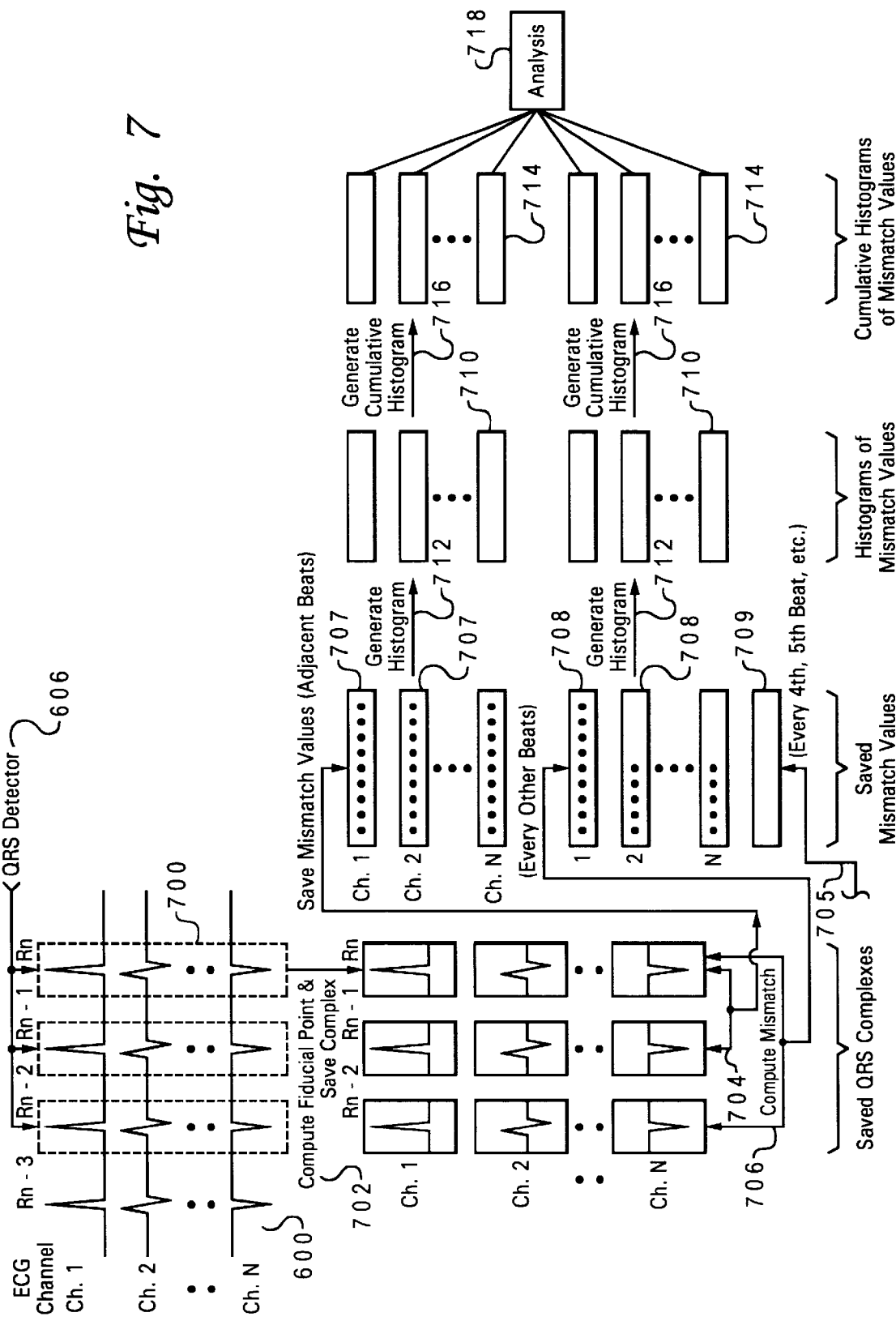
FIG. 7 is a high-level partially schematic diagram which illustrates pictographically how one embodiment of the present invention utilizes the above described methods and systems to achieve lead assessment.

Refer now to FIG. 7. FIG. 7 is a high-level partially schematic diagram which illustrates pictographically how one embodiment of the present invention utilizes the above described methods and systems to achieve lead assessment. Shown are input EKG data 600 waveforms in conjunction with the output of QRS complex detector 606 which indicates where the QRS complexes are contained in the waveforms on each lead in the input EKG data 600. In FIG. 7, the location of the QRS waveforms (that which is indicated by QRS complex detector 606) received from QRS complex detector indicated by the dashed-line rectangles 700.

Thereafter, shown is operation 702 which illustrates the use of the QRS complex detector 606 information to compute the fiducial point of each waveform and the saving of the QRS complexes with their fiducial points calculated.

Shown is that thereafter the stored QRS complexes can be utilized to compute the mismatch between successive (which, as has been explained above, "successive" can be interpreted to mean directly in sequence 704, or in alternative sequence 706, or in fourth, fifth, etc., sequence 705) QRS complexes on selected one or more leads. As is shown, the mismatch for those heartbeat waveforms in direct succession can be saved in adjacent beat bins 707, while the mismatch for those heartbeat QRS complexes in alternative succession can be saved in alternative beat bins 708, while the mismatch for those QRS complexes in fourth, fifth, etc. sequence can be saved in bin 709. (Fourth, fifth, etc. sequence 705 and beat bin 709 have been presented to make clear that such sequences can be used in addition to directly in sequence and alternatively in sequence waves, and consequently will not be discussed further. However, such fourth, fifth, etc. sequences could by used in a manner analogous to direct and alternative sequence, as discussed below.)

Thereafter, the saved mismatch information can be utilized to generate histograms of mismatch values 710 as is shown by generate histogram operations 712. Such computed histograms can then be utilized to generate cumulative histograms of mismatch values 714 as is shown by generate cumulative histogram operations 716.

Thereafter, cumulative histograms of mismatch values 714 are sent to analysis circuitry 718 which can analyze cumulative histograms of the one or more selected leads to assess the quality of the one or more selected leads and rank order the leads on the basis of said assessed quality.

Figure 8:
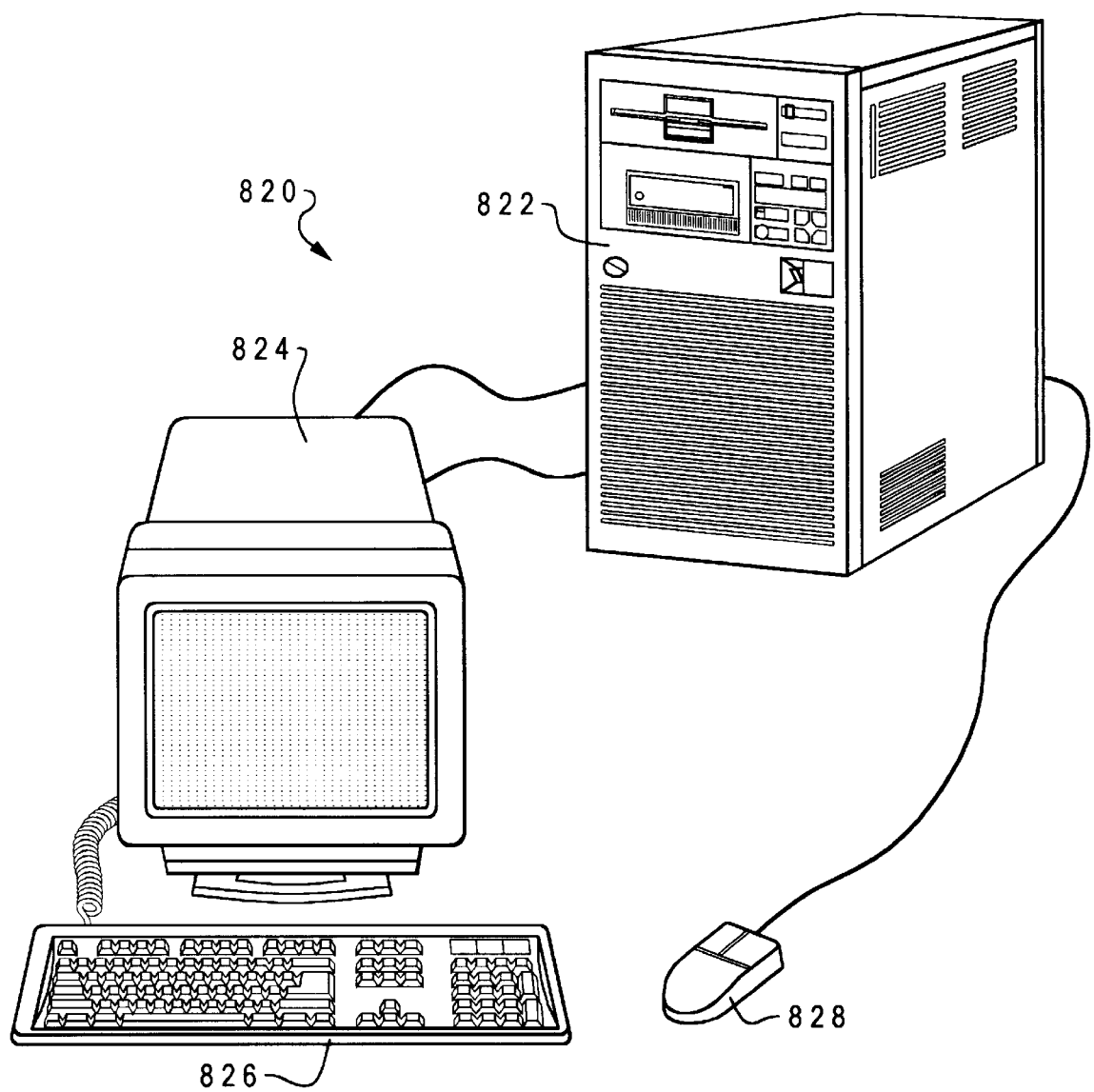
FIG. 8 depicts a pictorial representation of a data-processing system which can be utilized in accordance with the method and system of an illustrative embodiment of the present invention.

With reference now to the figures and in particular with reference now to FIG. 8, there is depicted a pictorial representation of a data-processing system which can be utilized in accordance with the method and system of an illustrative embodiment of the present invention. The method and system provided by an illustrative embodiment of the present invention can be implemented with the data-processing system depicted in FIG. 8. A computer 820 is depicted which includes a system unit 822, a video display terminal 824, a keyboard 826, and a mouse 828. Computer 820 may be implemented utilizing any suitably powerful computer, such as commercially available mainframe computers, minicomputers, or microcomputers.

Figure 9:
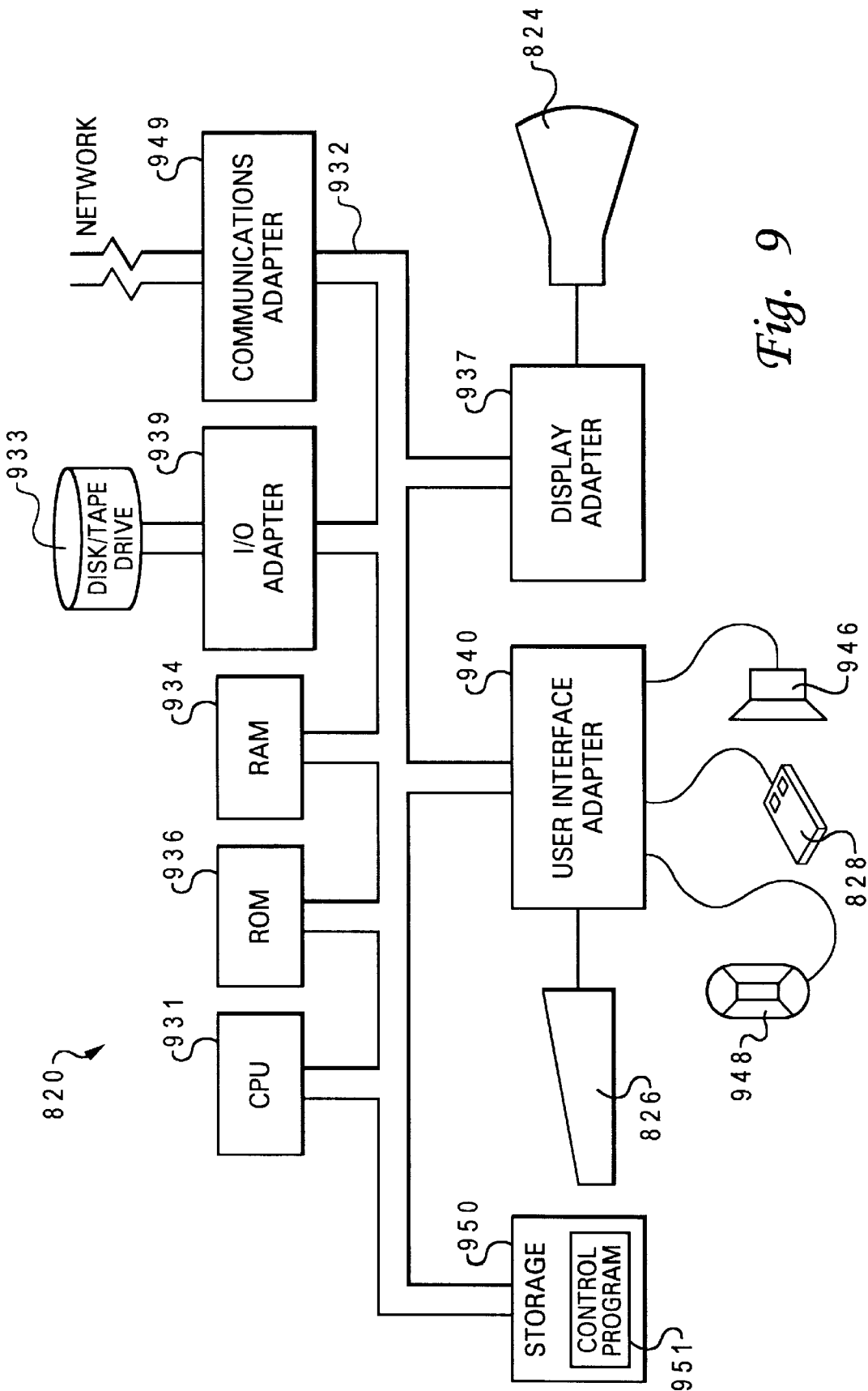
FIG. 9 is an illustration of a representative hardware environment which can be utilized in accordance with the method and system of an illustrative embodiment of the present invention.

FIG. 9 is an illustration of a representative hardware environment which can be utilized in accordance with the method and system of an illustrative embodiment of the present invention. FIG. 9 depicts selected components in computer 820 in which an illustrative embodiment of the present invention may be implemented. System unit 822 includes a Central Processing Unit ("CPU") 931, such as a conventional microprocessor, and a number of other units interconnected via system bus 932. Computer 820 includes random-access memory ("RAM") 934, read-only memory ("ROM") 936, display adapter 937 for connecting system bus 932 to video display terminal 824, and I/O adapter 939 for connecting peripheral devices (e.g., disk and tape drives 933) to system bus 932. Video display terminal 824 is the visual output of computer 820, which can be a CRT-based video display well-known in the art of computer hardware. However, with a portable or notebook-based computer, video display terminal 824 can be replaced with an LCD-based or a gas plasma-based flat-panel display. Computer 820 further includes user interface adapter 940 for connecting keyboard 826, mouse 828, speaker 946, microphone 948, and/or other user interface devices, such as a touch screen device (not shown), to system bus 932. Communications adapter 949 connects computer 820 to a data-processing network.

Any suitable machine-readable media may retain the method and system of an illustrative embodiment of the present invention, such as RAM 934, ROM 936, a magnetic diskette, magnetic tape, or optical disk (the last three being located in disk and tape drives 933). Any suitable operating system and associated graphical user interface may direct CPU 931. Other technologies can also be utilized in conjunction with CPU 931, such as touch-screen technology or human voice control. In addition, computer 820 includes a control program 951 which resides within computer storage 950. Control program 951 contains instructions that when executed on CPU 931 carries out the necessary operations described in relation to FIGS. 1–7 as described herein.

Those skilled in the art will appreciate that the hardware depicted in FIG. 9 may vary for specific applications. For example, other peripheral devices such as optical disk media, audio adapters, or chip programming devices, such as PAL or EPROM programming devices well-known in the art of computer hardware, and the like may be utilized in addition to or in place of the hardware already depicted.

As a final matter, it is important that while an illustrative embodiment of the present invention has been, and will continue to be, described in the context of a fully functional computing system, those skilled in the art will appreciate that the mechanisms of an illustrative embodiment of the present invention are capable of being distributed as a program product in a variety of forms, and that an illustrative embodiment of the present invention applies equally regardless of the particular type of signal bearing media used to actually carry out the distribution. Examples of signal bearing media include recordable type media such as floppy disks, hard disk drives, CD ROMs, and transmission type media such as digital and analogue communication links.

While an illustrative embodiment has been particularly shown and described, it will be understood by those skilled in the art that various changes in form and detail may be made therein without departing from the spirit and scope of the illustrative embodiment.

What is claimed is:

1. A method for characterizing the quality of signals indicative of heart function, where such signals indicative of heart function are derived from electrocardiographic measurements, said method comprising the steps of:

measuring one or more signals indicative of heart function;

in response to said step of measuring, creating a noise metric drawn upon physiological and non-physiological sources; and in response to said step of creating, designating the quality of the one or more signals indicative of heart function.

2. The method of claim 1, wherein said step of creating a noise metric further comprises the steps of:

calculating mismatch between successive QRS complexes in the one or more signals; and in response to said step of calculating, maintaining a cumulative record of the mismatch between successive QRS complexes in the one or more signals.

3. The method of claims 2, wherein said step of calculating mismatch further comprises calculating area differences between directly in sequence QRS complexes in the one or more signals.

4. The method claim 2, wherein said step of calculating mismatch further comprises the step of calculating area differences between indirectly in sequence QRS complexes in the one or more signals.

5. The method of claim 2, wherein said step of maintaining a cumulative record further comprises the step of recording a histogram of the mismatch between successive QRS complexes in the one or more area signals.

6. The method of claim 5, wherein said step of recording a histogram of the mismatch between successive QRS complexes in the one or more signals further comprises the step of recording a cumulative histogram of the mismatch between successive QRS complexes in the one or more signals.

7. The method of claim 5, wherein said step of designating the quality of the one or more signals further comprises the step of:

comparing one or more distributions of the histogram of the mismatch between successive QRS complexes in the one or more signals; and in response to said comparing, rank ordering the one or more measured signals.

8. The method of claim 7, wherein said step of rank ordering further comprises the step of ranking as higher quality those one or more signals whose distributions are centered about a smaller mean.

9. The method of claim 7, wherein said step of rank ordering further comprises the step of ranking as higher quality those one or more signals whose distributions are narrow.

10. The method of claim 1 further comprising the step of rank ordering the one or more signals.

11. A system for characterizing the quality of signals indicative of heart function, where such signals indicative of heart function are derived from electrocardiographic measurements, said system comprising:

means for measuring one or more signals indicative of heart function;

means, responsive to said means for measuring, for creating a noise metric drawn upon physiological and non-physiological sources; and means, responsive to said means for creating, for designating the quality of the one or more signals indicative of heart function.

12. The system of claim 11, wherein said means for creating a noise metric further comprises:

means for calculating mismatch between successive QRS complexes in the one or more signals; and means, responsive to said means for calculating, for maintaining a cumulative record of the mismatch between successive QRS complexes in the one or more signals.

13. The system of claim 12, wherein said means for calculating mismatch further comprises means for calculating area differences between directly in sequence QRS complexes in the one or more signals.

14. The system of claim 12, wherein said means for calculating mismatch further comprises means for calculating area differences between indirectly in sequence QRS complexes in the one or more signals.

15. The system of claim 12, wherein said means for maintaining a cumulative record further comprises the step of recording a histogram of the mismatch between successive QRS complexes in the one or more area signals.

16. The system of claim 15, wherein said means for recording a histogram of the mismatch between successive QRS complexes in the one or more signals further comprises means for recording a cumulative histogram of the mismatch between successive QRS complexes in the one or more signals.

17. The system of claim 15, wherein said means for designating the quality of the one or more signals further comprises:

means for comparing one or more distributions of the histogram of the mismatch between successive QRS complexes in the one or more signals; and means, responsive to said means for comparing, for rank ordering the one or more measured signals.

18. The system of claim 17, wherein said means for rank ordering further comprises means for ranking as higher quality those one or more signals whose distributions are centered about a smaller mean.

19. The system of claim 17, wherein said means for rank ordering further comprises means for ranking as higher quality those one or more signals whose distributions are narrow.

20. The system of claim 11 further comprising means for rank ordering the one or more signals.

* * * * *